United States Patent
Lin

(10) Patent No.: US 6,602,729 B2
(45) Date of Patent: Aug. 5, 2003

(54) PULSE VOLTAGE BREAKDOWN (VBD) TECHNIQUE FOR INLINE GATE OXIDE RELIABILITY MONITORING

(75) Inventor: Chaun Lin, Poughquag, NY (US)

(73) Assignee: Infineon Technologies AG, Munich (DE)

(*) Notice: Subject to any disclaimer, the term of this patent is extended or adjusted under 35 U.S.C. 154(b) by 0 days.

(21) Appl. No.: 09/905,386

(22) Filed: Jul. 13, 2001

(65) Prior Publication Data

US 2003/0013214 A1 Jan. 16, 2003

(51) Int. Cl.$^7$ .......................... H01L 21/66; G01R 31/01
(52) U.S. Cl. .......................................... 438/17; 324/551
(58) Field of Search .............................. 438/14, 17, 18; 324/551, 158.1, 500, 765, 555, 537; 700/121; 702/57, 58, 59, 81, 84

(56) References Cited

U.S. PATENT DOCUMENTS 5,420,513 A * 5/1995 Kimura ....................... 324/551
6,429,677 B1 * 8/2002 Montrose ................. 324/158.1

* cited by examiner

Primary Examiner—Evan Pert

(57) ABSTRACT

Disclosed is a method of testing a dielectric, comprising setting a reference current below a breakdown current of the dielectric, applying a stress voltage to the dielectric below a breakdown voltage of the dielectric and measuring a stress current resulting therefrom, incrementally increasing said stress voltage until said measured stress current exceeds said reference current.

10 Claims, 6 Drawing Sheets

PULSE VOLTAGE BREAKDOWN (VBD) TECHNIQUE FOR INLINE GATE OXIDE RELIABILITY MONITORING

FIELD OF THE INVENTION

This invention relates to the destructive inline testing of semiconductor gate oxides by the use of pulse voltage breakdown testing.

BACKGROUND OF THE INVENTION

The inline monitoring of very thin gate oxides is a difficult, but highly desirable procedure for reducing manufacturing rejects in the semiconductor industry. Accuracy is required to ensure good chips are not wrongly rejected and defective chips are not mistakenly passed by. Accuracy, however, must be traded off against speed, so as not to hold up the production rate.

In the manufacture of semiconductor devices, various layers of material are deposited on the semiconductor substrate followed by removal of unwanted portions of each layer. The procedures used to deposit the layers, such as chemical vapor deposition in sputtering conditions, among others, as well as the procedures used to remove unwanted material, such as such as chemical, plasma, or reactive ion etching among others, may cause damage to underlying structures, particularly very thin structures, such as gate oxides.

Metal-oxide semiconductor (MOS) transistors rely upon a thin silicon oxide gate separating the gate from the channel. It is desirable to deposit these gates as thinly as possible to reduce the voltage required to activate the channel, thereby reducing the overall power requirements of the devices while simultaneously increasing their speed. Damage to the gate oxide layer may result in unacceptable current leakage from the gate to the channel, thereby resulting in reduced device performance or even total failure.

The manufacturer would therefore desire to test and monitor the gate quality of the gates coming down the assembly line so as to detect faults in the manufacturing process and to remove defective chips before further processing wasted upon them.

The current art has many procedures to test gates, some destructive, such as in electron microscopy examination wherein the wafer under examination must be cross-sectioned, and that require special circuitry be included in the wafer.

A destructive inline procedure that may or may not require additional testing circuitry on the wafer itself is pulse, or ramped voltage breakdown testing. Typically, a ramped sweep voltage is placed across the gate oxide by connecting probes to the gate and the semiconductor substrate layer, just beneath the gate oxide. A typical procedure would be to ramp the voltage from a base voltage (e.g., about 1.5 volts) to an increasingly higher stress voltage and take two current measurements, one at the base voltage and one at the stress voltage. This procedure is repeated, increasing the stress voltage each time in some small increment, usually 0.1 volts, until a maximum stress voltage is reached, usually about 7 volts. Each current measurement will generally take about 20 microseconds and there are two such measurements per ramping, so the total sweep will take at least 2*20*(7−1.5)10.1 =2200 ins, not taking into account the time it takes for the voltage to ramp up to the stress voltage or to come back down to the base voltage. The procedure is accurate enough, but time consuming.

What is needed is a faster pulse voltage breakdown test with equal or greater accuracy than the available art.

SUMMARY OF THE INVENTION

Disclosed is a method of testing a dielectric, comprising setting a reference current below a breakdown current of the dielectric, applying a stress voltage to the dielectric below a breakdown voltage of the dielectric and measuring a stress current resulting therefrom, incrementally increasing said stress voltage until said measured stress current exceeds said reference current.

DETAILED DESCRIPTION OF PREFERRED EMBODIMENTS

Figure 1:
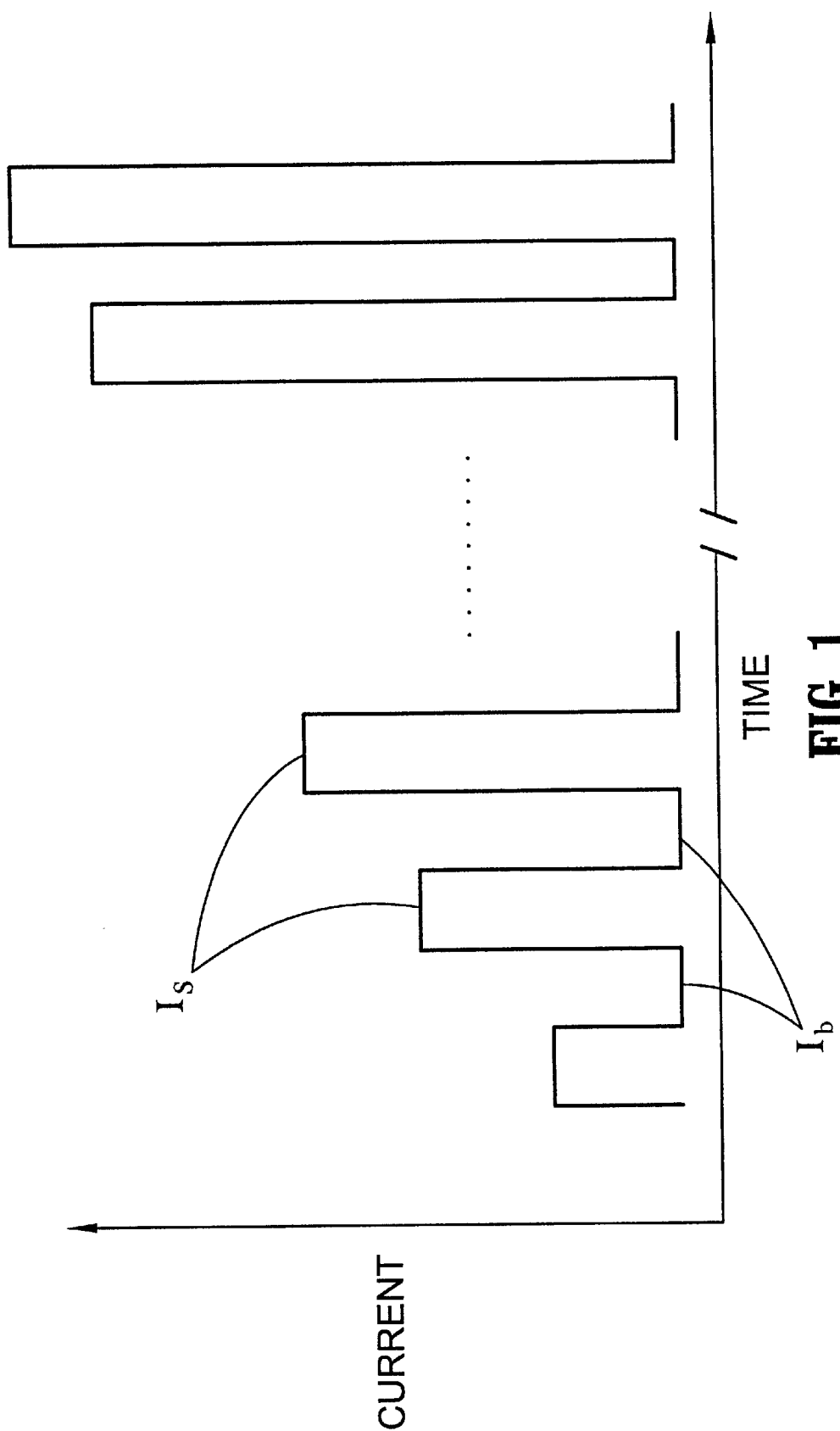
FIG. 1 is a graph of current versus time in accordance with the prior art.

FIG. 1 shows a graph of current versus time for a typical pulse voltage breakdown test of the prior art. Typically, a ramped sweep voltage is placed across a dielectric, such as a gate oxide, using commercially available testing devices well known in the art. The voltage is applied by connecting probes across the dielectric. If this cannot be done directly, then a special testing structure will typically be added to all or a sampling of the manufactured wafers to permit access to the dielectric by the probes.

Figure 6:
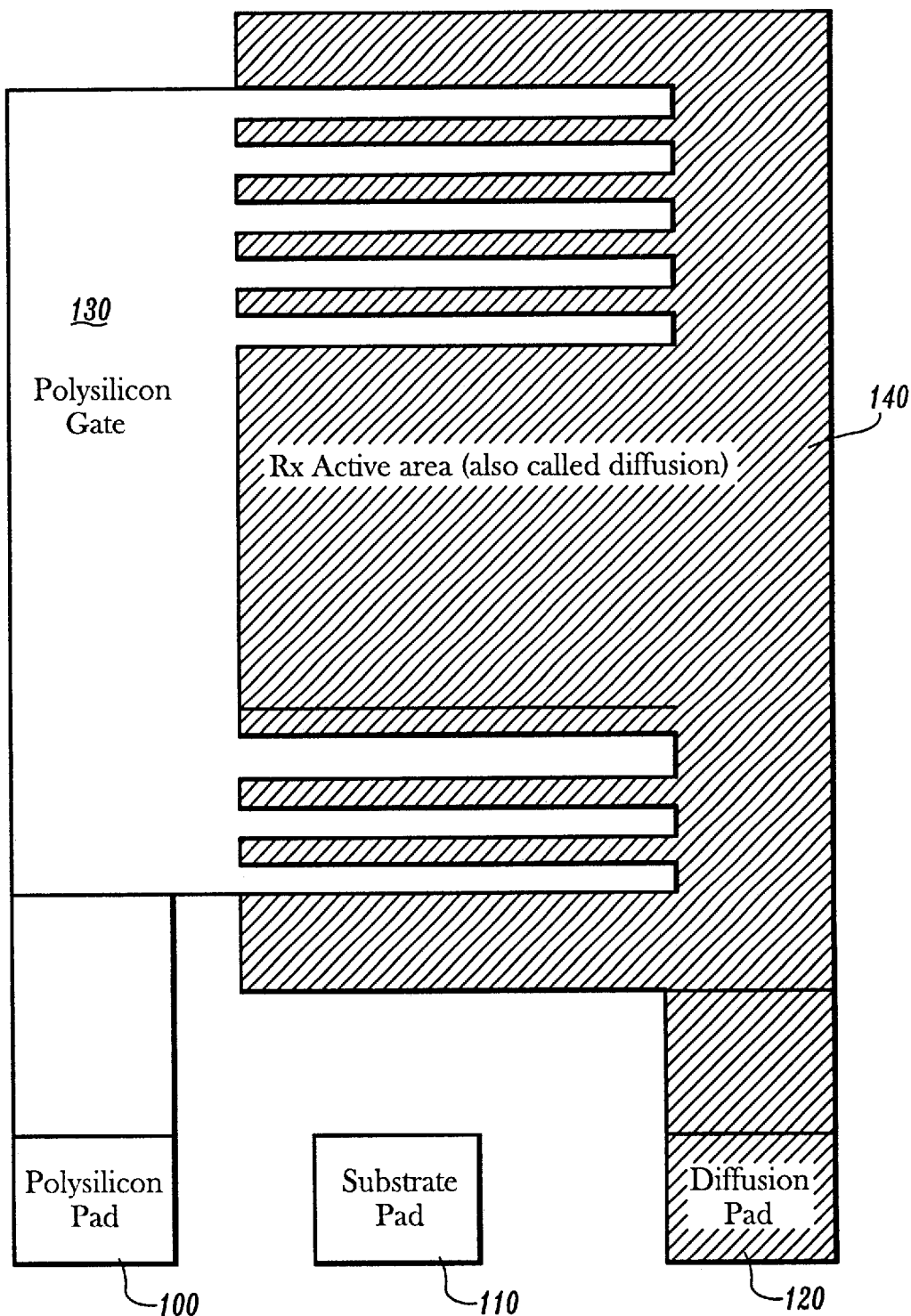
FIG. 6 is a diagram of a typical test structure.

A typical testing structure is shown in FIG. 6 in layout view. For a semiconductor gate oxide, the probes will be electrically connected to the gate 130 and to the active area 140 just beneath the gate oxide. A third grounding probe will usually be connected to the semiconductor substrate to ground it. To do this, a special testing structure may be required to provide a gate pad 100, an active area (or diffusion) pad 120, and a substrate pad 110 to which the probes may be contacted.

During testing, the voltage is ramped from a base voltage $V_b$ to an increasingly higher stress voltage $V_s$ and two current measurements are taken, a base current $I_b$ measurement at the base voltage and a stress current $I_s$ measurement at the stress voltage. The base voltage will typically be selected to be substantially equal to the operating voltage of the dielectric (e.g., about 1.5 volts). This procedure is repeated, increasing the stress voltage each time by some small increment $V_s$, often 0.1 volts, until a maximum stress voltage $V_{smax}$ is reached. The maximum stress voltage is selected to be high enough to ensure that breakdown will occur, but not so high as to waste valuable testing time, which for today's gate oxide technology will usually be about 7 volts. If each current measurement takes a minimum of about 20 microseconds and there are two such measurements per ramping, the total sweep will take at least 2*20*(7−1.5)/0.1=2200 ms, not taking into account the time it takes for the voltage to ramp up to the stress voltage or to come back down to the base voltage. The current measurement period is chosen to be long enough for the stress voltage to stabilize and the actual time it takes to read the current will vary according to current, smaller currents requiring more time. The procedure is accurate enough, but time consuming. The purpose of measuring the base current over and over again is to detect the situation where the dielectric fails completely, that is to say that the dielectric is physically destroyed, at which point testing may be brought to a halt.

Figure 2:
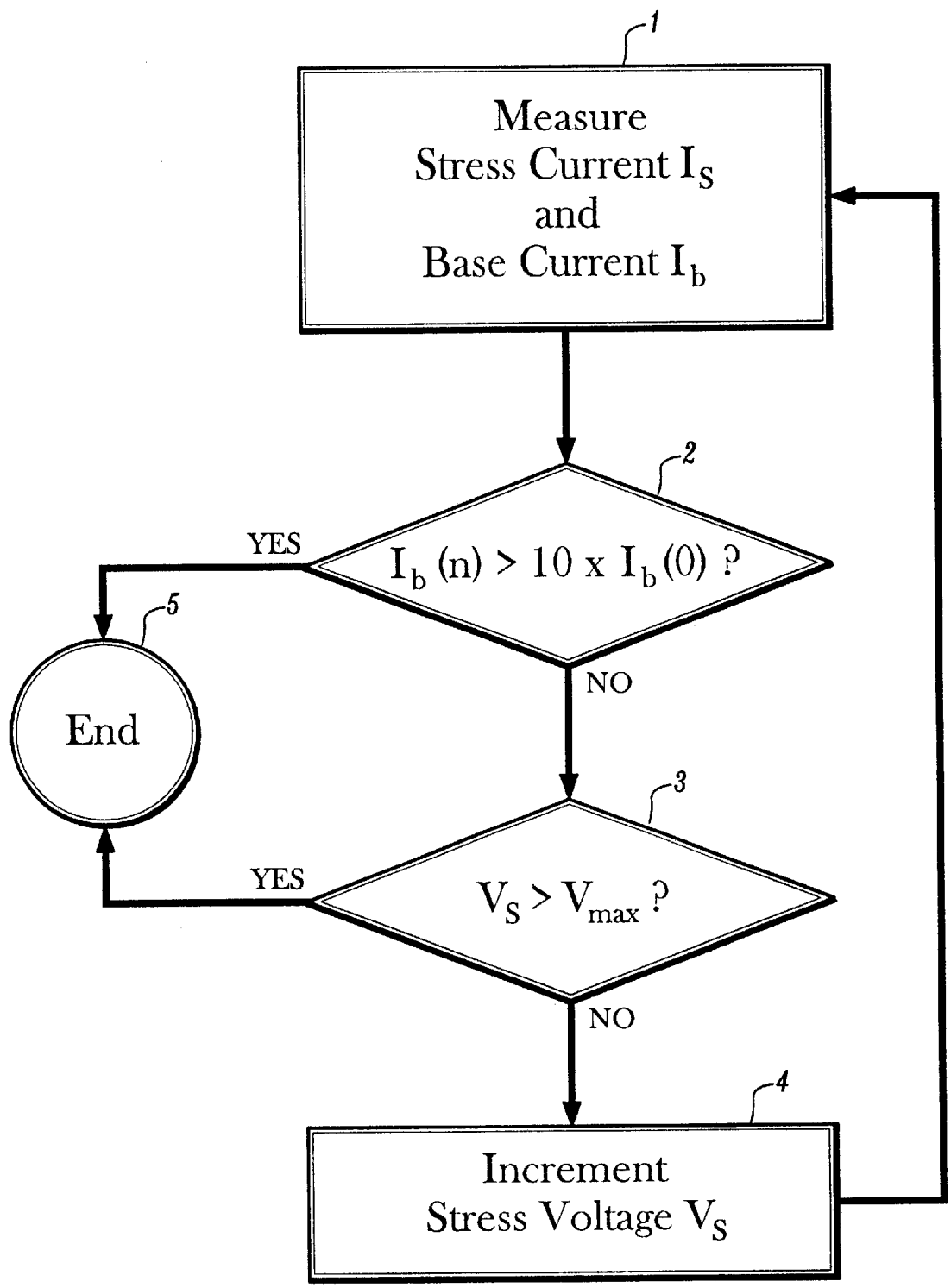
FIG. 2 is a flowchart of a conventional testing method in accordance with FIG. 1.
Figure 3:
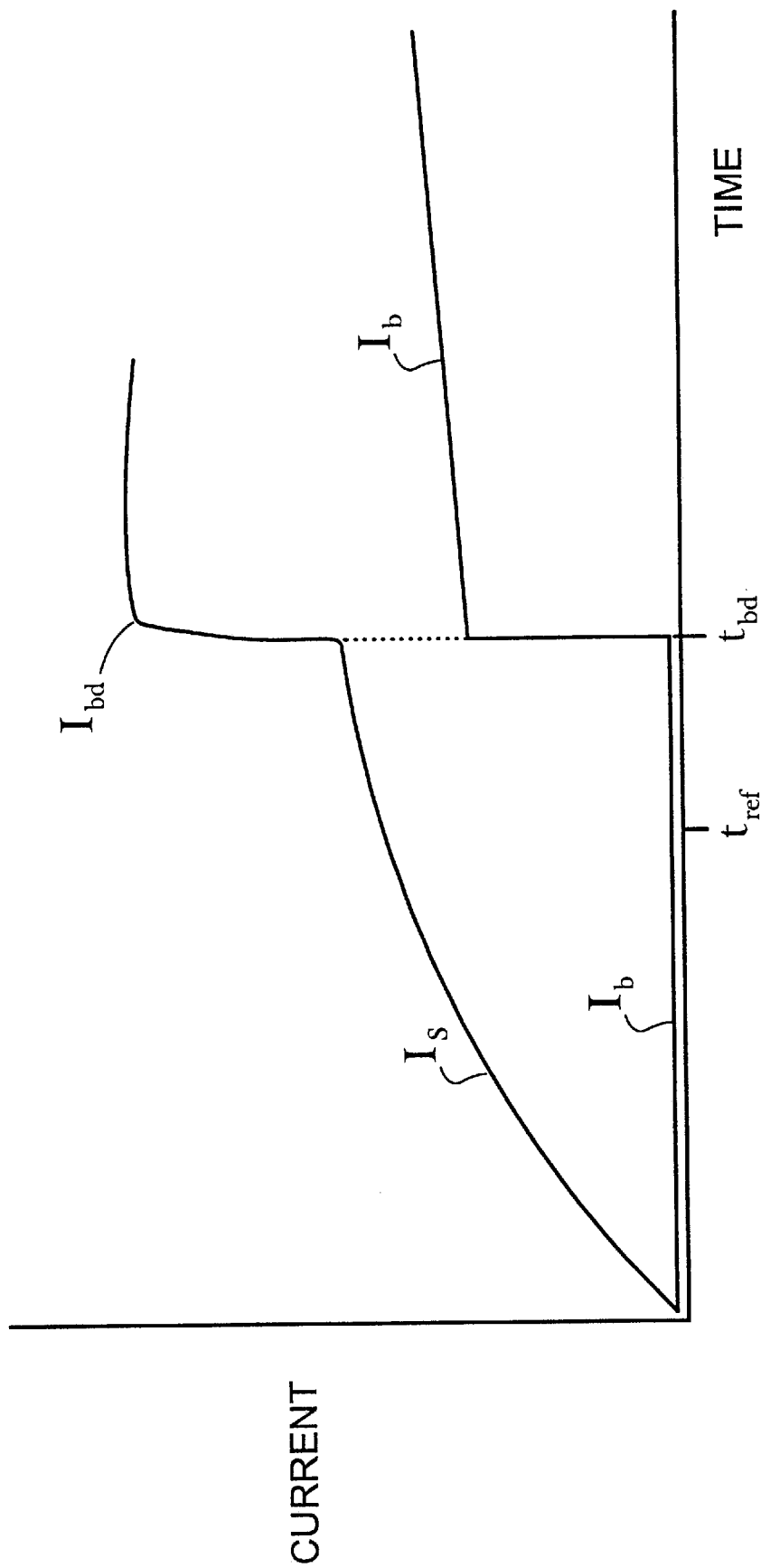
FIG. 3 is a graph of current versus time in accordance with the invention and the prior art.

FIG. 2 is a flowchart of a prior art method that would generate the graphs of FIGS. 1 and 3. At node 1, stress currents $I_s$ and base currents $I_b$ are measured. At decision node 2, if the measured base current is more than a certain multiple of the initially measured base current $I_b(0)$ (e.g., by a factor of ten in this example), then a breakdown is confirmed and the procedure may end 5. Otherwise, control flows to decision node 3 and, if the stress voltage $V_s$ is not yet at maximum $V_{max}$, then the stress voltage is incremented at node 4 and the loop continues.

FIG. 3 shows a graph of the measured stress and base currents over time. At some point during the testing, the stress voltage $V_s$ will reach the breakdown voltage $V_{bd}$ of the dielectric at time $t_{bd}$ as revealed by a substantial increase in current $I_{bd}$ over the stress current $I_s$. Usually, this will coincide with a substantial increase (e.g., typically an order of magnitude) in base current $I_b$, thereby confirming the destruction of the dielectric.

Figure 5:
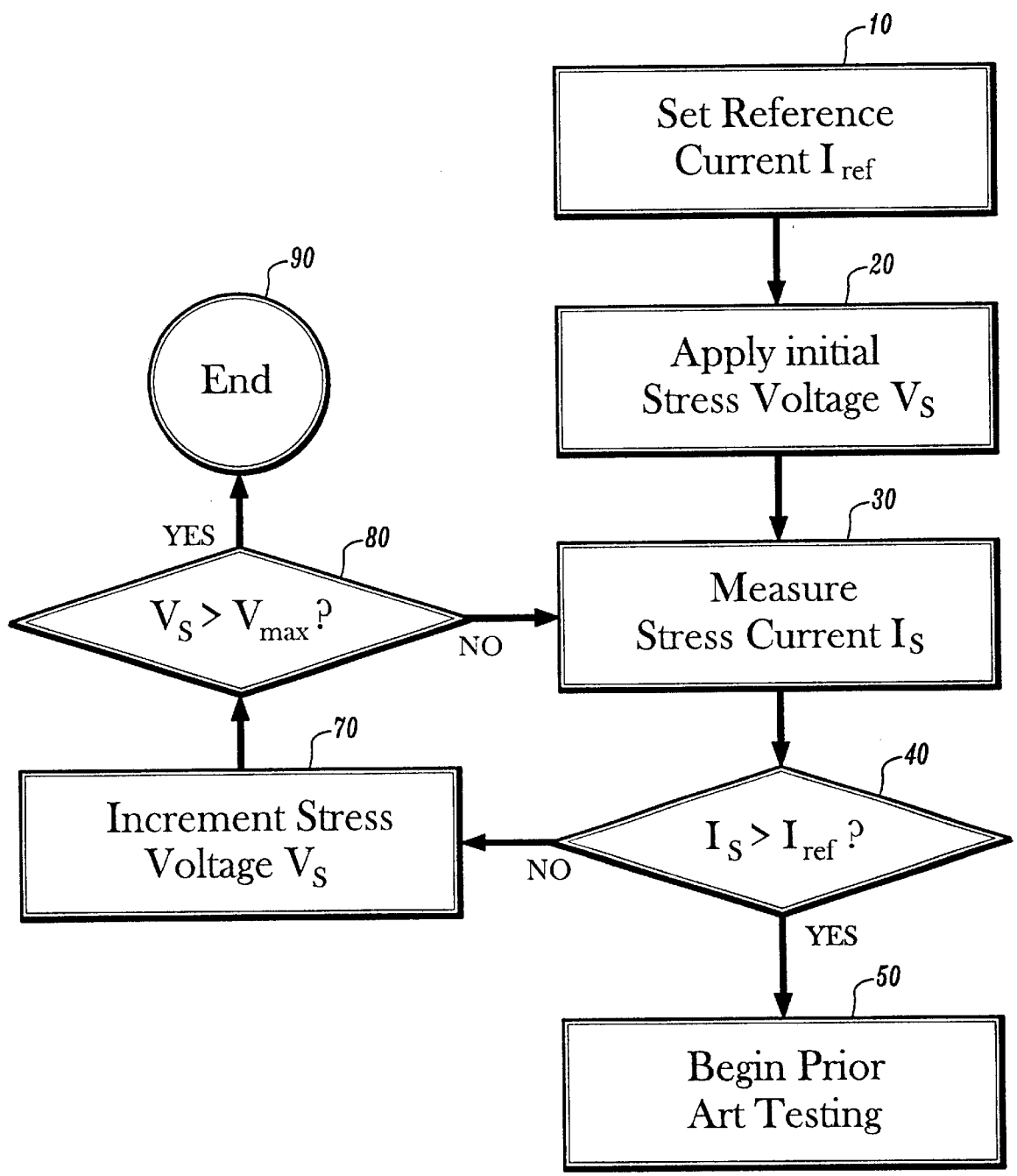
FIG. 5 is a flowchart of an embodiment of the invention.

Referring to FIG. 5, a flowchart of an embodiment of the procedure of the invention is shown. In the embodiment shown, process flow begins at node 10, wherein the reference current $I_{ref}$ is set. This will be a value chosen to be below the breakdown current $I_{bd}$ of the dielectric, meaning the current measured at the breakdown voltage $V_{bd}$, but greater than the expected base current so as to avoid wasting time on unnecessary early measurement of the base current, such that:

$$I_b < I_{ref} < I_{bd} \quad (1)$$

At nodes 20 and 30 in the flowchart, the testing device is set to the initial stress voltage $V_s$ and the stress current $I_s$ is measured. The measured stress current $I_s$ is then compared to the reference current $I_{ref}$ at decision node 40. Note that node 10 need not necessarily precede the first run through nodes 30 and 40, but will be required before the first instance of node 40. At node 40, if the measured stress current $I_s$ is found to be greater than the reference current $I_{ref}$, then the system reverts to the prior art method of testing at node 50, meaning the method as described with respect to FIGS. 1 and 2, or any other suitable method of testing as appropriate or desired. If, however, the measured stress current $I_s$ is the same or lower than the reference current $I_{ref}$, then the stress voltage is incremented by an amount $V_s$ at node 70 and the procedure continues through the testing loop. Nodes 80 and 90 may be optionally provided for preventing the situation where the maximum stress voltage was set too low to cause a breakdown. Alternatively, if decision node 80 finds that the stress voltage $V_s$ is greater than the maximum stress voltage $V_{max}$, the system can be programmed to increment the maximum stress voltage $V_{max}$ by some amount.

Figure 4:
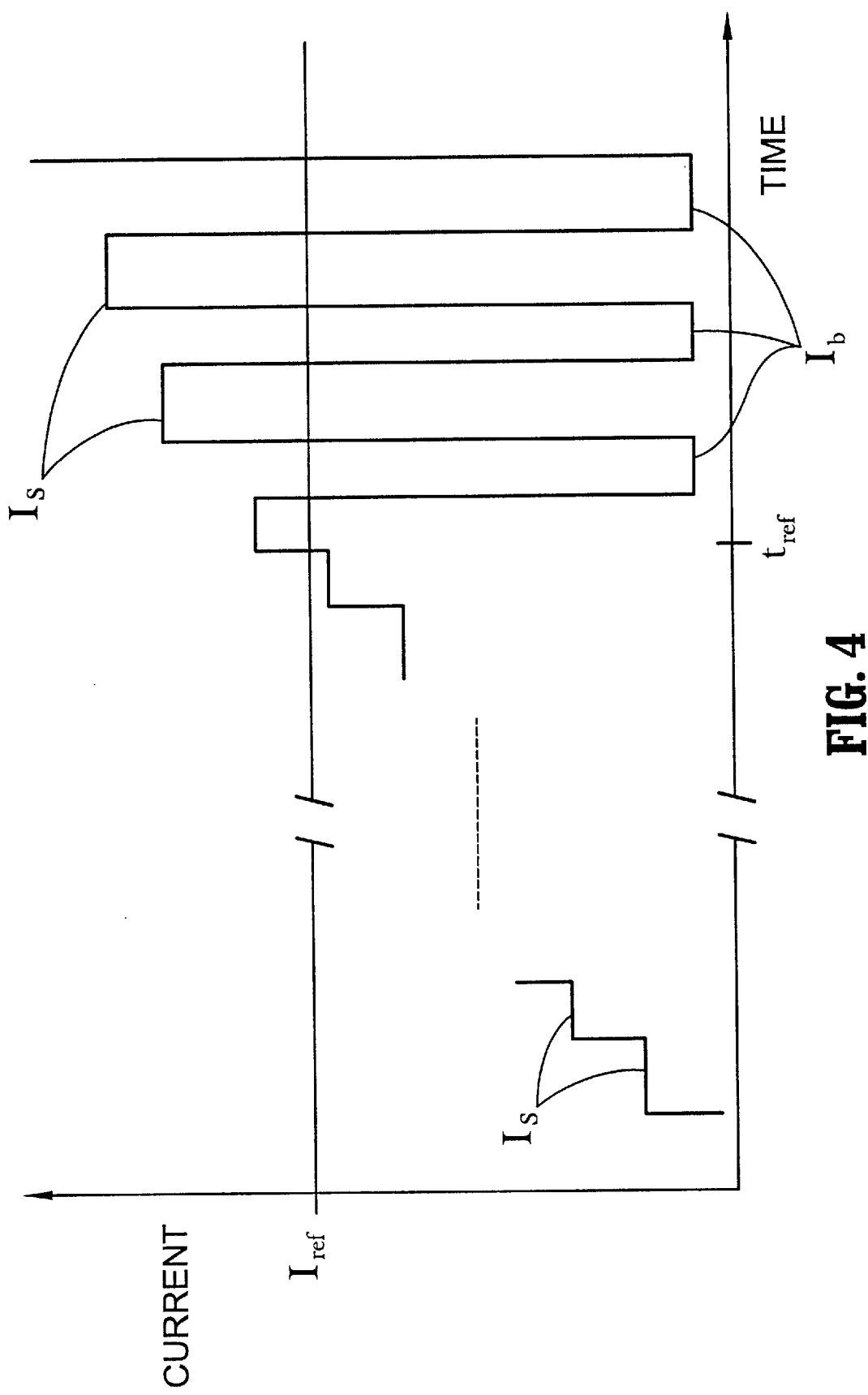
FIG. 4 is a graph of current versus time in accordance with the invention.

Referring to FIG. 4, we see a graph of the inventive method showing measured currents plotted against time. As can be seen, much time is saved as the stress voltage $V_s$ is rapidly incremented up to deliver the reference current $I_{ref}$ before the prior art method is initiated at time $t_{ref}$.

Note that a graph of stress current versus time for the method of the invention is identical to that of the prior art as shown in FIG. 3 except that $I_b$ is not tested until $I_s > I_{ref}$, thereby effecting a substantial time savings and increasing throughput on the assembly line. Comparing the examples of FIGS. 1 and 4, one may expect the testing time to be reduced on average by 10% to 30% by the invention, typically about 20%.

Of course, though the examples described herein have been with respect to an MOS dielectric, it is to be understood that the teachings of the invention are generalizable to any dielectric, semiconductor or otherwise.

The invention may be implemented on any programmable testing device such as are commercially available and known in the art. Such devices are commonly available, for example, from KLA-Tencor Corporation for the testing of semiconductors. Implementation is effected by embodying the steps of the invention upon a machine-readable media that then may be executed to control the testing device to perform the method of the invention. It is also understood that the teachings of the invention are generalizable to the testing of any dielectric and not limited to those in the semiconductor art.

It is to be understood that all physical quantities disclosed herein, unless explicitly indicated otherwise, are not to be construed as exactly equal to the quantity disclosed, but rather as about equal to the quantity disclosed. Further, the mere absence of a qualifier such as "about" or the like, is not to be construed as an explicit indication that any such disclosed physical quantity is an exact quantity, irrespective of whether such qualifiers are used with respect to any other physical quantities disclosed herein.

While preferred embodiments have been shown and described, various modifications and substitutions may be made thereto without departing from the spirit and scope of the invention. Accordingly, it is to be understood that the present invention has been described by way of illustration only, and such illustrations and embodiments as have been disclosed herein are not to be construed as limiting to the claims.

What is claimed is:

1. A method of testing a dielectric, comprising:
   setting a reference current below a breakdown current of the dielectric and higher than an expected base current of the dielectric;
   applying a stress voltage to the dielectric below a breakdown voltage of the dielectric and measuring a stress current resulting therefrom;
   incrementally increasing said stress voltage until said measured stress current exceeds said reference current;
   measuring a base current of the dielectric after said measured stress current exceeds said reference current; and
   incrementally increasing said stress voltage until said measured base current indicates said stress voltage equals or exceeds said breakdown voltage.

2. The method of claim 1 further comprising:
   measuring a base current of the dielectric after said measured stress current exceeds said reference current;
   incrementally increasing said stress voltage until said measured stress current indicates said stress voltage equals or exceeds said breakdown voltage.

3. The method of claim 1 wherein said indication that said stress voltage equals or exceeds said breakdown voltage is when said measured base current increases by an order of magnitude upon a said incrementation of said stress voltage.

4. The method of claim 1 wherein said indication that said stress voltage equals or exceeds said breakdown voltage is when said measured stress current increases by an order of magnitude upon a said incrementation of said stress voltage.

5. The method of claim 1 wherein said expected base current is equal to a current that would be measured at about the standard operating voltage of the dielectric.

6. A program storage device readable by machine, tangibly embodying a program of instructions executable by the machine to perform a method for testing a dielectric, said method comprising:

setting a reference current below a breakdown current of the dielectric and higher than an expected base current of the dielectric;

applying a stress voltage to the dielectric below a breakdown voltage of the dielectric and measuring a stress current resulting therefrom;

incrementally increasing said stress voltage until said measured stress current exceeds said reference current;

measuring a base current of the dielectric after said measured stress current exceeds said reference current; and incrementally increasing said stress voltage until said measured base current indicates said stress voltage equals or exceeds said breakdown voltage.

7. The program storage device of claim 6 wherein said indication that said stress voltage equals or exceeds said breakdown voltage is when said measured base current increases by an order of magnitude upon a said incrementation of said stress voltage.

8. The program storage device of claim 6 further comprising:

incrementally increasing said stress voltage until said measured stress current indicates said stress voltage equals or exceeds said breakdown voltage.

9. The program storage device of claim 6 wherein said indication that said stress voltage equals or exceeds said breakdown voltage is when said measured stress current increases by an order of magnitude upon a said incrementation of said stress voltage.

10. The program storage device of claim 6, wherein said expected base current is equal to a current that would be measured at about the standard operating voltage of the dielectric.

* * * * *